(12) United States Patent
Park et al.

(10) Patent No.: US 11,331,081 B2
(45) Date of Patent: May 17, 2022

(54) MEDICAL IMAGING APPARATUS, MEDICAL IMAGING APPARATUS CONTROL METHOD, AND COMPUTER PROGRAM PRODUCT

(71) Applicant: SAMSUNG MEDISON CO., LTD., Hongcheon-gun (KR)

(72) Inventors: Jonggeun Park, Seongnam-si (KR); Jungho Kim, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 483 days.

(21) Appl. No.: 16/354,571

(22) Filed: Mar. 15, 2019

(65) Prior Publication Data

US 2019/0282214 A1     Sep. 19, 2019

(30) Foreign Application Priority Data

Mar. 16, 2018   (KR) ........................ 10-2018-0031126

(51) Int. Cl.
*A61B 8/00*     (2006.01)
*A61B 8/08*     (2006.01)
(Continued)

(52) U.S. Cl.
CPC .......... *A61B 8/5292* (2013.01); *A61B 5/0035* (2013.01); *A61B 5/055* (2013.01);
(Continued)

(58) Field of Classification Search
CPC combination set(s) only.
See application file for complete search history.

(56) References Cited

U.S. PATENT DOCUMENTS 9,161,734 B2    10/2015  Vincent et al.
2004/0264756 A1  12/2004  Spahn
(Continued)

FOREIGN PATENT DOCUMENTS

KR          10-1562942 B1    10/2015
KR       10-2016-0052305 A    5/2016
(Continued)

OTHER PUBLICATIONS

Communication dated Aug. 21, 2019 by the European Patent Office in counterpart European Patent Application No. 19161521.0.

*Primary Examiner* — Joel F Brutus
(74) *Attorney, Agent, or Firm* — Sughrue Mion, PLLC

(57) ABSTRACT

Provided is a medical imaging apparatus including a storage configured to store training data and an optimization coefficient; at least one processor configured to identify at least one image feature value from an input medical image, and to identify a value of at least one parameter of the medical imaging apparatus, based on the at least one image feature value and the optimization coefficient, by using a neural network processor; an output interface configured to output a resultant image generated based on the value of the at least one parameter; and an input interface configured to receive a first control input of adjusting the value of the at least one parameter, wherein the at least one processor is further configured to update the optimization coefficient by performing training using the training data and the first control input.

18 Claims, 12 Drawing Sheets

(51) Int. Cl.
  *G06T 7/11* (2017.01)
  *A61B 5/00* (2006.01)
  *A61B 5/055* (2006.01)
  *G16H 30/40* (2018.01)
  *G16H 40/63* (2018.01)
  *A61B 6/03* (2006.01)
  *A61B 6/00* (2006.01)
  *A61B 8/14* (2006.01)
  *G06T 7/00* (2017.01)

(52) U.S. Cl.
  CPC ............ *A61B 8/469* (2013.01); *A61B 8/5207* (2013.01); *G06T 7/11* (2017.01); *G16H 30/40* (2018.01); *G16H 40/63* (2018.01); *A61B 6/03* (2013.01); *A61B 6/566* (2013.01); *A61B 8/14* (2013.01); *A61B 8/463* (2013.01); *A61B 8/465* (2013.01); *G06T 7/0012* (2013.01); *G06T 2207/10081* (2013.01); *G06T 2207/20081* (2013.01)

(56) References Cited

U.S. PATENT DOCUMENTS

| | | |
|---|---|---|
| 2006/0079778 A1 | 4/2006 | Mo et al. |
| 2015/0297186 A1 | 10/2015 | Yang et al. |
| 2016/0120508 A1 | 5/2016 | Kim et al. |
| 2016/0209995 A1* | 7/2016 | Jeon .................. G16H 40/63 |
| 2016/0283680 A1 | 9/2016 | Deng et al. |
| 2016/0310111 A1 | 10/2016 | Cho et al. |
| 2016/0345936 A1 | 12/2016 | Cho et al. |
| 2017/0103512 A1 | 4/2017 | Mailhe et al. |
| 2017/0156698 A1 | 6/2017 | Park et al. |

FOREIGN PATENT DOCUMENTS

| | | |
|---|---|---|
| KR | 10-2016-0140237 A | 12/2016 |
| KR | 10-2017-0077208 A | 7/2017 |

* cited by examiner

FIG. 7
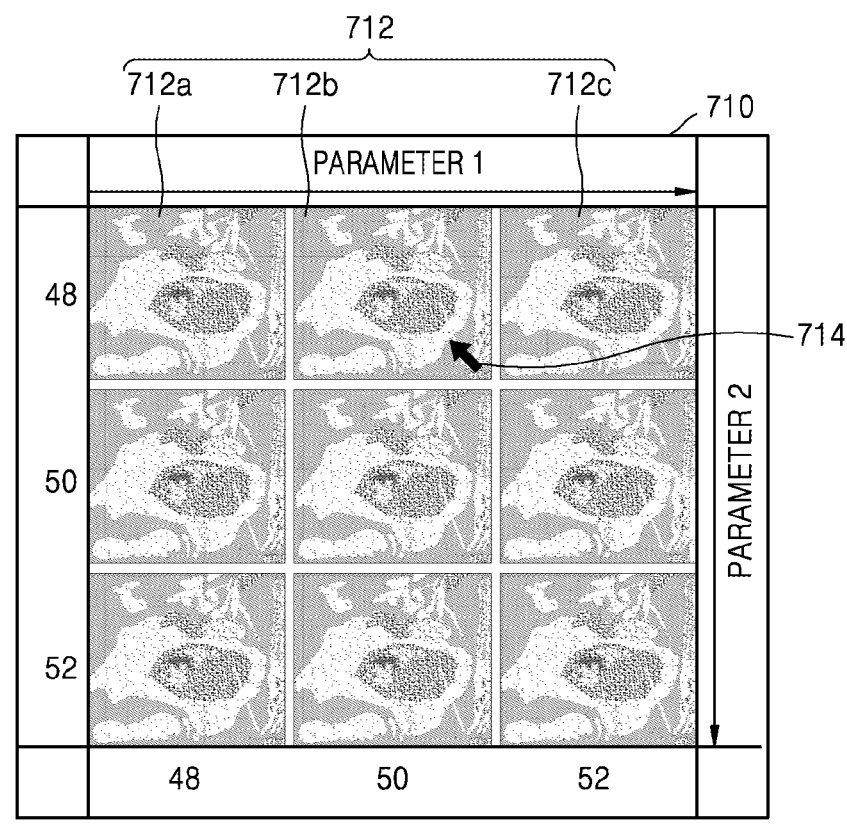
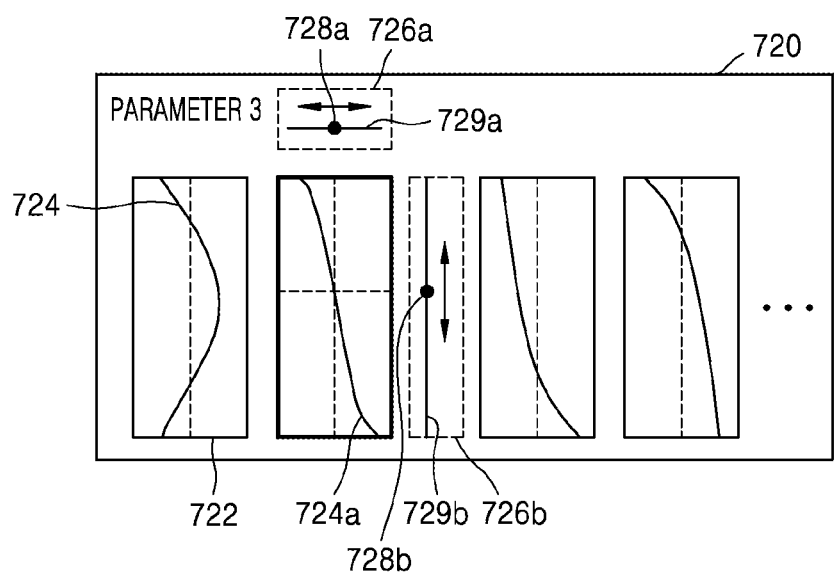

MEDICAL IMAGING APPARATUS, MEDICAL IMAGING APPARATUS CONTROL METHOD, AND COMPUTER PROGRAM PRODUCT

CROSS-REFERENCE TO RELATED APPLICATION(S)

This application is based on and claims priority under 35 U.S.C. § 119 to Korean Patent Application No. 10-2018-0031126, filed on Mar. 16, 2018, in the Korean Intellectual Property Office, the disclosure of which is incorporated by reference herein in its entirety.

BACKGROUND

1. Field

The disclosure relates to a medical imaging apparatus, a medical imaging apparatus control method, and a computer program product including a computer-readable storage medium storing computer program codes to perform the medical imaging apparatus control method.

2. Description of Related Art

A medical imaging apparatus is an apparatus configured to scan an object and then obtain volume data or a tomography image of the object, and examples of the medical imaging apparatus include a computed tomography (CT) apparatus, a magnetic resonance imaging apparatus, an X-ray imaging apparatus, or the like. In a process of scanning an object, a process of processing obtained raw data and image data, and a process of reconstructing a medical image, the medical imaging apparatus sets various parameters. The setting of parameters may be automatically performed by the medical imaging apparatus or may be performed according to a user input. However, because the parameters can be variously set according to scanned environments, it is difficult to set an appropriate parameter for a certain situation.

SUMMARY

Embodiments of the disclosure are provided to improve a function of automatically setting parameters in a medical imaging apparatus.

Embodiments of the disclosure are provided to automatically determine an appropriate parameter, in consideration of a user, a use environment, an apparatus used by the user, patient information, a protocol, or the like.

Embodiments of the disclosure are provided to decrease a need for development manpower, a development period, and development costs of a medical imaging apparatus by simplifying initial settings of the medical imaging apparatus.

Additional aspects will be set forth in part in the description which follows and, in part, will be apparent from the description, or may be learned by practice of the presented embodiments.

In accordance with an aspect of the disclosure, a medical imaging apparatus includes a storage configured to store training data and an optimization coefficient; at least one processor configured to identify at least one image feature value from an input medical image, and to identify a value of at least one parameter of the medical imaging apparatus, based on the at least one image feature value and the optimization coefficient, by using a neural network processor; an output interface configured to output a resultant image generated based on the value of the at least one parameter; and an input interface configured to receive a first control input of adjusting the value of the at least one parameter, wherein the at least one processor is further configured to update the optimization coefficient by performing training using the training data and the first control input.

The at least one processor may be further configured to identify the value of the at least one parameter by using at least one user feature value of the medical imaging apparatus as an input value to be input to the neural network processor.

The at least one processor may be further configured to identify the value of the at least one parameter by using a use environment feature value of the medical imaging apparatus as an input value to be input to the neural network processor.

The at least one processor may be further configured to identify the value of the at least one parameter by using an apparatus feature value corresponding to the medical imaging apparatus as an input value to be input to the neural network processor.

The at least one processor may be further configured to identify the value of the at least one parameter by using a patient feature value corresponding to an object of the medical imaging apparatus as an input value to be input to the neural network processor.

The at least one processor may be further configured to identify the value of the at least one parameter by using a scan control feature value of the medical imaging apparatus as an input value to be input to the neural network processor, wherein the scan control feature value includes at least one of a protocol, a type of a region of interest (ROI), and a position of the ROI, or a combination thereof.

The at least one processor may be further configured to provide a graphical user interface (GUI) configured to receive the first control input, wherein an interface view of the GUI includes a plurality of candidate medical images generated by using respective candidate values with respect to the at least one parameter, and wherein, in response to the first control input of selecting one of the plurality of candidate medical images, the at least one processor is further configured to identify a candidate value as the value of the at least one parameter, the candidate value corresponding to the selected candidate medical image.

The at least one parameter may include a first parameter corresponding to a set of a plurality of values, wherein the interface view includes a plurality of candidate graphs indicating the set of the plurality of values corresponding to the first parameter, and wherein, in response to the first control signal of selecting one of the plurality of candidate graphs, the at least one processor is further configured to identify the selected candidate graph as the value of the at least one parameter.

The optimization coefficient may include respective optimization coefficients with respect to a plurality of values of a first feature, wherein the first feature is one of a user feature, a use environment feature, an apparatus feature, a patient feature, and a scan control feature.

The at least one processor may be further configured to store, in the storage, the updated optimization coefficient, and to store, as the training data in the storage, the at least one image feature value and the at least one parameter which corresponds to the first control input.

In accordance with another aspect of the disclosure, a medical imaging apparatus control method includes identifying at least one image feature value from an input medical image; identifying a value of at least one parameter of the medical imaging apparatus, based on the at least one image feature value and an optimization coefficient, by using a neural network processor; outputting a resultant image generated based on the value of the at least one parameter; receiving a first control input of adjusting the value of the at least one parameter; and updating the optimization coefficient by performing training using the training data and the first control input.

In accordance with another aspect of the disclosure, a computer program product includes a computer-readable storage medium storing computer program codes for performing a medical imaging apparatus control method, the medical imaging apparatus control method including identifying at least one image feature value from an input medical image; identifying a value of at least one parameter of the medical imaging apparatus, based on the at least one image feature value and an optimization coefficient, by using a neural network processor; outputting a resultant image generated based on the value of the at least one parameter; receiving a first control input of adjusting the value of the at least one parameter; and updating the optimization coefficient by performing training using training data and the first control input.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 7 illustrates a graphical user interface (GUI) view according to an embodiment;

DETAILED DESCRIPTION

Figure 1:
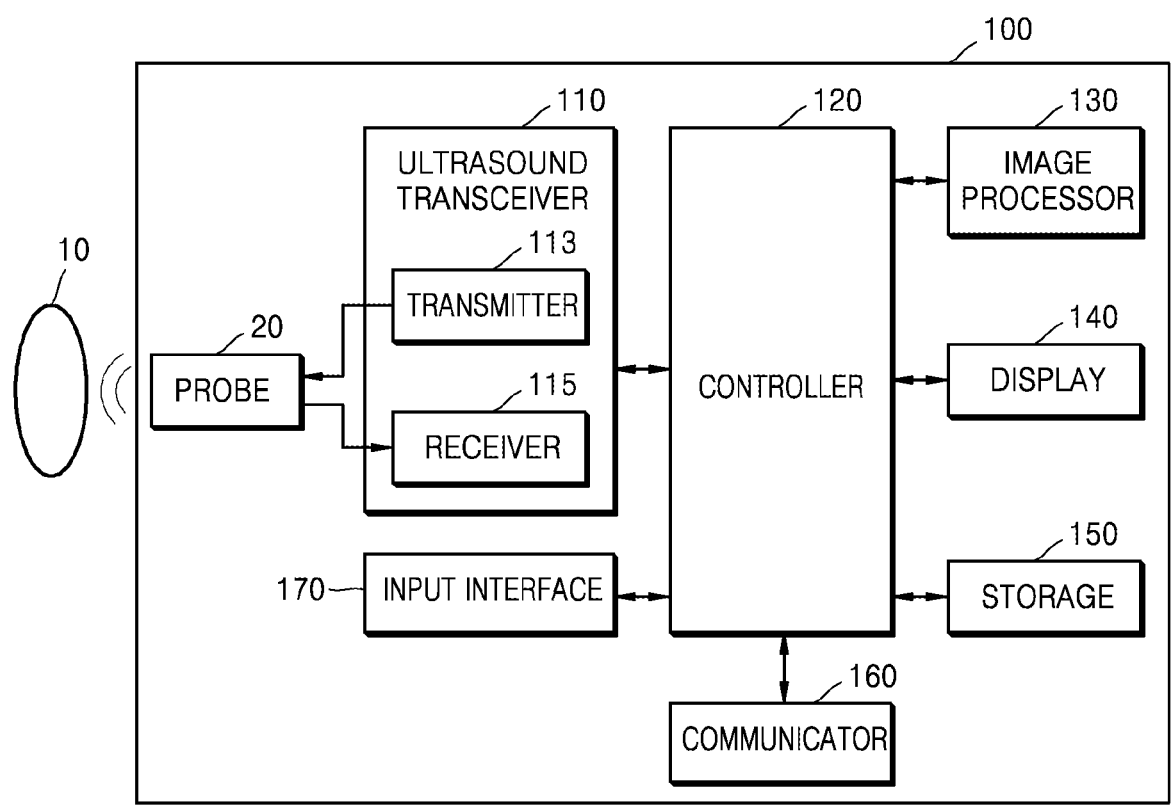
FIG. 1 is a block diagram illustrating a configuration of an ultrasound diagnosis apparatus, according to an embodiment.

The principles of embodiments of the disclosure will now be described and embodiments thereof will now be provided to clearly define the scope of claims and for one of ordinary skill in the art to be able to perform the present. The present disclosure may, however, be embodied in many different forms and should not be construed as being limited to the embodiments set forth herein.

Throughout the specification, like reference numerals denote like elements. Not all elements of the embodiments are described in the specification, and general features in the art or redundant features among the embodiments are omitted. Throughout the specification, a term such as "module" or "unit" may be implemented as one of or a combination of at least two of software, hardware, and firmware. In some embodiments, a plurality of modules or a plurality of units may be implemented as one element, or a module or a unit may include a plurality of elements.

As used herein, the term "and/or" includes any and all combinations of one or more of the associated listed items. Expressions such as "at least one of," when preceding a list of elements, modify the entire list of elements and do not modify the individual elements of the list.

Hereinafter, embodiments of the present disclosure will now be described with reference to the accompanying drawings.

In embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

Hereinafter, embodiments will now be described with reference to the accompanying drawings.

In the present disclosure, a medical imaging apparatus may be embodied as an MRI apparatus, a CT apparatus, an ultrasound diagnosis apparatus, or an X-ray apparatus. In the present disclosure, it is assumed that the medical imaging apparatus is an ultrasound diagnosis apparatus, but embodiments of the present disclosure are not limited to an ultrasound diagnosis apparatus.

FIG. 1 is a block diagram illustrating a configuration of an ultrasound diagnosis apparatus 100, according to an embodiment.

Referring to FIG. 1, the ultrasound diagnosis apparatus 100 may include a probe 20, an ultrasound transceiver 110, a controller 120, an image processor 130, a display 140, a storage 150, a communicator 160, and an input interface 170.

The ultrasound diagnosis apparatus 100 may be of a cart-type or portable-type ultrasound diagnosis apparatus, that is portable, moveable, mobile, or hand-held. Examples of the portable-type ultrasound diagnosis apparatus 100 may include a smartphone, a laptop computer, a personal digital assistant (PDA), a tablet personal computer (PC), or the like, each of which may include a probe and a software application, but embodiments are not limited thereto.

The probe 20 may include a plurality of transducers. The plurality of transducers may transmit ultrasound signals to an object 10, in response to transmitting signals received by the probe 20, from a transmitter 113. The plurality of transducers may receive ultrasound signals reflected from the object 10 so as to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked in a wired or wireless manner. In addition, the ultrasound diagnosis apparatus 100 may include one or more probes 20 according to embodiments.

The controller 120 may control the transmitter 113 to generate transmitting signals to be applied to each of the plurality of transducers, based on a position and a focal point of the plurality of transducers included in the probe 20.

The controller 120 may control a receiver 115 to generate ultrasound data by converting reception signals received from the probe 20 from analogue to digital signals and summing the reception signals converted into digital form, based on the position and the focal point of the plurality of transducers.

The image processor 130 may generate an ultrasound image by using ultrasound data generated by the ultrasound receiver 115.

The display 140 may display the generated ultrasound image and various pieces of information processed by the ultrasound diagnosis apparatus 100. The ultrasound diagnosis apparatus 100 may include one or more displays 140 according to embodiments. Also, the display 140 may include a touchscreen in combination with a touch panel.

The controller 120 may control operations of the ultrasound diagnosis apparatus 100 and flow of signals between internal elements of the ultrasound diagnosis apparatus 100. The controller 120 may include a memory configured to store a program or data to perform functions of the ultrasound diagnosis apparatus 100, and a processor and/or a microprocessor (not shown) to process the program or data. For example, the controller 120 may control operations of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smartphones, tablet PCs, wearable devices, or the like via the communicator 160.

The communicator 160 may include at least one element capable of communicating with the external apparatuses. For example, the communicator 160 may include at least one of a short-range communication module, a wired communication module, and a wireless communication module.

The communicator 160 may exchange a control signal and data with the external apparatuses.

The storage 150 may store various data or programs for driving and controlling the ultrasound diagnosis apparatus 100, input and/or output ultrasound data, obtained ultrasound images, applications, or the like.

The input interface 170 may receive a user input to control the ultrasound diagnosis apparatus 100. Examples of the user input may include an input of manipulating a button, a keypad, a mouse, a trackball, a jog switch, knob, or the like, an input of touching a touchpad or a touchscreen, a voice input, a motion input, and a bioinformation input, for example, iris recognition or fingerprint recognition, but the present disclosure is not limited thereto.

An example of the ultrasound diagnosis apparatus 100 according to an embodiment will be described below with reference to FIGS. 2A, 2B, and 2C.

Figure 2:
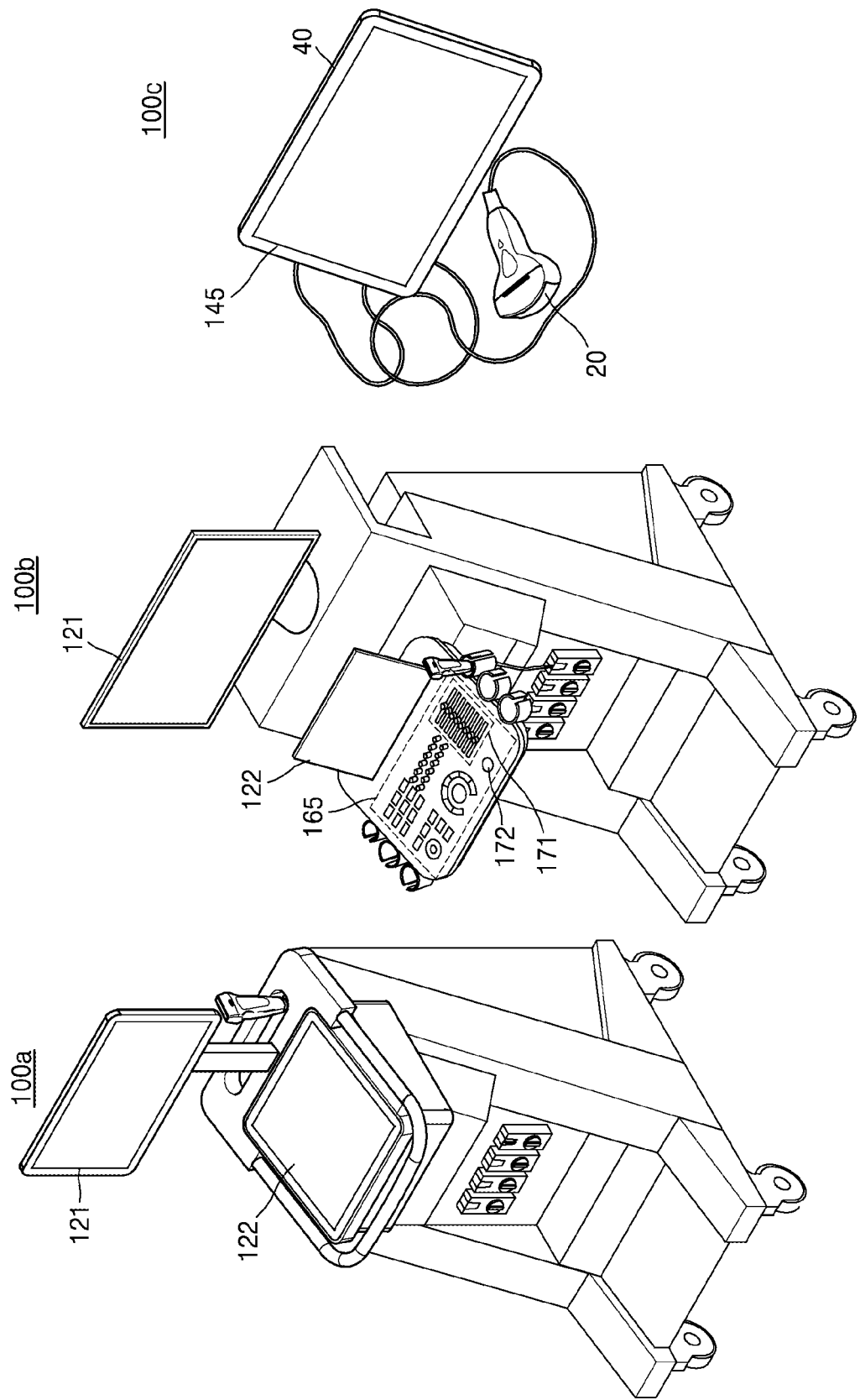
FIGS. 2A, 2B, and 2C are diagrams illustrating an ultrasound diagnosis apparatus according to an embodiment.

FIGS. 2A, 2B, and 2C are diagrams illustrating an ultrasound diagnosis apparatus according to an embodiment.

Referring to FIGS. 2A and 2B, the ultrasound diagnosis apparatuses 100a and 100b may each include a main display 121 and a sub-display 122. At least one of the main display 121 and the sub-display 122 may include a touchscreen. The main display 121 and the sub-display 122 may display ultrasound images and/or various information processed by the ultrasound diagnosis apparatuses 100a and 100b. The main display 121 and the sub-display 122 may provide graphical user interfaces (GUIs), thereby receiving user inputs of data to control the ultrasound diagnosis apparatuses 100a and 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatuses 100a and 100b may control the display of the ultrasound image on the main display 121 by using the input control data.

Referring to FIG. 2B, the ultrasound diagnosis apparatus 100b may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100b may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100c may include a portable device. An example of the portable ultrasound diagnosis apparatus 100c may include, for example, smart phones including probes and applications, laptop computers, personal digital assistants (PDAs), or tablet PCs, but an exemplary embodiment is not limited thereto.

The ultrasound diagnosis apparatus 100c may include the probe 20 and a main body 40. The main body 40 may include a touchscreen 145. The touchscreen 145 may display an ultrasound image, various pieces of information processed by the ultrasound diagnosis apparatus 100c, and a GUI.

Figure 3:
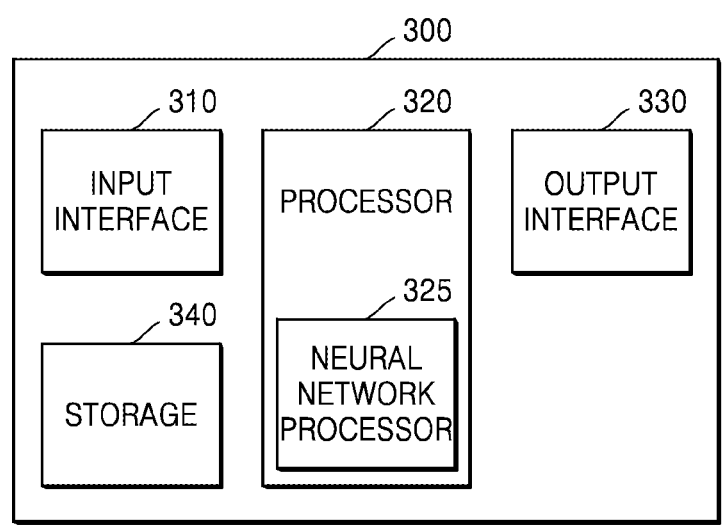
FIG. 3 is a diagram illustrating a configuration of a medical imaging apparatus according to an embodiment.

FIG. 3 is a diagram illustrating a configuration of a medical imaging apparatus 300 according to an embodiment.

The medical imaging apparatus 300 includes an input interface 310, a processor 320, an output interface 330, and a storage 340. The processor 320 may include one or more processors and may include a neural network processor 325.

The medical imaging apparatus 300 and a scan unit to scan an object may be embodied in one body or may be separately embodied. For example, the medical imaging apparatus 300 and the ultrasound diagnosis apparatus 100 may be embodied in one body, or the medical imaging apparatus 300 may be embodied as a computer or a portable terminal configured to communicate with the ultrasound diagnosis apparatus 100. Also, according to an embodiment, the medical imaging apparatus 300 may be embodied as a workstation arranged outside a scan room of a CT imaging apparatus, an MRI apparatus, or an X-ray apparatus.

The medical imaging apparatus 300 may automatically set a parameter used by the medical imaging apparatus 300 or the scan unit. In the present disclosure, the parameter indicates a parameter for setting components of the medical imaging apparatus 300 or the scan unit, or a parameter used in processing image data. The parameter may include a gain of signal processing, a Digital Radiography (DR) index of a detector, or the like. Also, the parameter may include a TGC value, a lateral gain compensation (LGC) value, or the like of the ultrasound diagnosis apparatus 100. Also, the parameter may include a window level (WL), a window width (WW), or the like of the ultrasound diagnosis apparatus 100.

The input interface 310 receives a medical image. The medical image may be raw data or a reconstructed image. Also, the medical image may be an ultrasound image, a CT image, an MRI image, or an X-ray image.

According to the present embodiment, the input interface 310 may be implemented as a communicator. The communicator may receive the medical image from the scan unit of the scan room or an external apparatus. The input interface 310 may receive the medical image by using wired or wireless communication.

According to another embodiment, the input interface 310 may be embodied as a scan unit. For example, the scan unit may be embodied as an ultrasound probe, an X-ray generator and an X-ray detector of a CT imaging apparatus, a scanner of an MRI apparatus, or an X-ray generator and an X-ray detector of an X-ray apparatus. The input interface 310 may obtain raw data of an imaged object.

Also, the input interface 310 may receive a control input from a user. According to an embodiment, the input interface 310 may receive a first control input of setting a parameter from the user. The input interface 310 may be embodied as a keyboard, a mouse, a touchscreen, a touch pad, a wheel, a knob, or the like.

The processor 320 may control all operations of the medical imaging apparatus 300. The processor 320 may include one or more processors and may include the neural network processor 325. According to an embodiment, the neural network processor 325 may be embodied as a separate chip. The neural network processor 325 may include a neural network.

The processor 320 may identify at least one image feature value from an input medical image. The at least one image feature value indicates a value obtained from the input medical image, and may include a mean, a contrast, a standard deviation, sharpness, a view type, or the like. The processor 320 may obtain an image feature value of raw data or reconstructed data of an input medical image. The image feature value may configure a feature vector corresponding to the input medical image. The feature vector may correspond to a set of a plurality of image feature values.

According to an embodiment, when a control signal requesting execution of an auto scan mode is input via the input interface 310, the processor 320 may perform an operation of estimating an optimal parameter.

The processor 320 obtains a parameter value of an input medical image, based on an optimization coefficient with respect to at least one parameter stored in the storage 340. The optimization coefficient is a coefficient for calculating at least one parameter value from at least one feature value. A function of calculating a parameter value from at least one feature value may be expressed as various forms of the function, and for example, the function may be expressed as various forms of the function, the forms including a linear function, a quadratic function, an exponential function, a logarithmic function, or the like. According to an embodiment, the optimization coefficient may indicate a weight with respect to each node of a neural network processor.

The processor 320 may estimate at least one optimization coefficient by using new training data and pre-trained data stored in the storage 340. The pre-trained data and the new training data may include a feature vector and a parameter value corresponding thereto. The new training data may be obtained based on a first control signal of setting at least one parameter value. For example, when the first control signal of setting an A parameter as a second value is input, a value of the A parameter corresponding to a feature vector of an input medical image is set as the second value, and a case in which the A parameter is set as the second value with respect to the feature vector may be stored as the new training data.

Also, the processor 320 may update the optimization coefficient with respect to the at least one parameter stored in the storage 340, based on the first control signal of setting the at least one parameter value. For example, when an optimization coefficient with respect to the A parameter is stored as a first set in the storage 340, and the first control signal of setting the A parameter as the second value is input, the processor 320 may update the optimization coefficient with respect to the A parameter, based on the first control signal. In detail, the processor 320 may use, as the new training data, the case of setting the A parameter as the second value, may reflect the new training data thereto, and then may update the optimization coefficient with respect to the A parameter as the second set. According to an embodiment, whenever the first control signal of setting the value of the A parameter is input, the stored optimization coefficient is updated in real time, therefore, even when a preset number of training data is not accumulated, an optimization coefficient may be immediately updated, and an optimal result based on user preference may be obtained.

When the processor 320 calculates an optimization coefficient with respect to a parameter, the processor 320 may use a method such as a linear least squares method, deep learning, or the like. For example, to estimate the optimization coefficient, the processor 320 may estimate the optimization coefficient by which a least square value with respect to the parameter value corresponding to the first control signal is calculated when the feature vector is inserted thereto. As another example, the processor 320 may estimate, by using deep learning, the optimization coefficient by which the parameter value corresponding to the first control signal is calculated with respect to the feature vector.

When the first control signal of setting at least one parameter value is input, the processor 320 may set the at least one parameter value based on the first control signal, may update the medical image by using the set parameter value, and may display the updated medical image. For example, the processor 320 may obtain a resultant medical image while the A parameter is set as a first value, and when the first control signal of setting the A parameter as the second value is input while the obtained resultant medical image is displayed on a display, the processor 320 may re-obtain a resultant medical image by setting the A parameter as the second value, and may update the displayed medical image to the re-obtained resultant medical image.

The output interface 330 may output a resultant medical image. According to an embodiment, the output interface 330 may include a display and may display the resultant medical image on the display. According to another embodiment, the output interface 330 may include a communicator, and may transmit the resultant medical image to an external apparatus by using the communicator. The external apparatus may include a user terminal, an external server, a console, or the like. Examples of the user terminal may include a smartphone, a tablet PC, a PC, or the like.

The output interface 330 may include the display and may display a GUI on the display. The output interface 330 may display the resultant medical image on the GUI. Also, the output interface 330 may provide a GUI for receiving an input of the first control signal.

The storage 340 may store the pre-trained data, the new training data, and the optimization coefficient with respect to at least one parameter.

Figure 4:
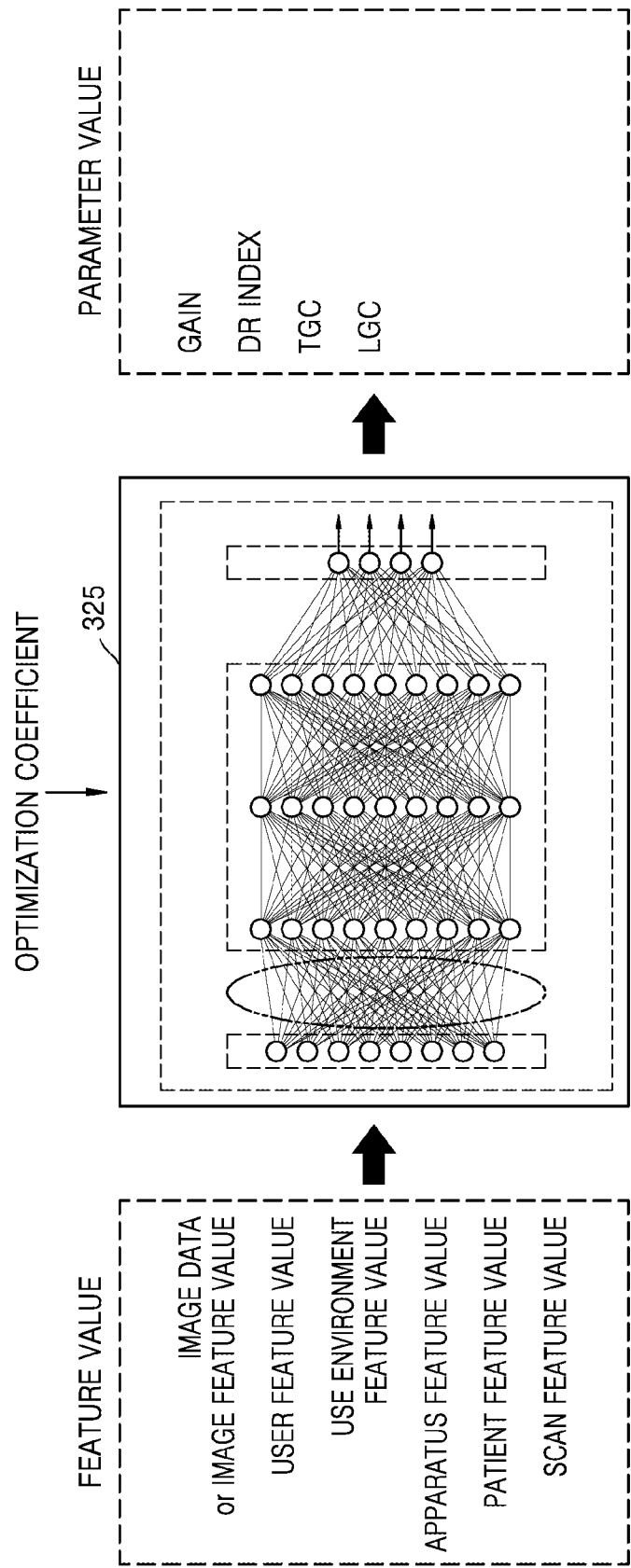
FIG. 4 is a diagram illustrating a process of estimating a parameter value, according to an embodiment.

FIG. 4 is a diagram illustrating a process of estimating a parameter value, according to an embodiment.

According to an embodiment, the medical imaging apparatus 300 may estimate at least one parameter value from a feature vector by using the neural network processor 325.

The feature vector may include a plurality of feature values. For example, the feature vector may include at least one of an image feature value, a user feature value, a use environment feature value, an apparatus feature value, a patient feature value, and a scan feature value, or a combination thereof. According to an embodiment, raw data with respect to a feature value may be input to the neural network processor 325, and then the neural network processor 325 may calculate the feature value from the raw data and may estimate a parameter value by using the calculated feature value. For example, image data may be input to the neural network processor 325, and the neural network processor 325 may extract an image feature value from the image data and then may obtain a parameter value by using the image feature value.

The combination of feature values included in the feature vector may vary according to each case. For example, in a case where an ultrasound image is obtained, an image feature value is obtained from the obtained ultrasound image, the medical imaging apparatus 300 calculates a first parameter value from a first feature vector including the image feature value, and then a user feature value is input, a second feature vector including the image feature value and the user feature value may be input again to the neural network processor 325, and the neural network processor 325 may calculate a second parameter value corresponding to the second feature vector.

The neural network processor 325 may include a plurality of layers and a plurality of nodes. The plurality of layers may include at least one of a input layer, the hidden layer, and the output layer. An optimization coefficient may be input to the neural network processor 325 and may be applied to the plurality of layers and the plurality of nodes.

The neural network processor 325 may estimate at least one parameter value from the input feature vector. For example, the neural network processor 325 may estimate at least one of a gain, a DR index, a TGC value, and an LGC value, or a combination thereof.

The user feature value may include a user's job and user preference. The user's job may be classified into a doctor, a radiologic technologist, a nurse, a normal person, etc. The user preference may indicate preferences respectively corresponding to a plurality of pieces of identification information, based on user identification information. For example, information indicating that a user A prefers a gain of 50 and a user B prefers a gain of 48 may be considered as a feature value.

The user feature value may be obtained by obtaining the user identification information and using user information stored in the storage 340. According to an embodiment, the medical imaging apparatus 300 may obtain the user feature value from a user input via the input interface 310 or an input from an external apparatus. For example, the processor 320 may provide a GUI for receiving the user feature value and may obtain the user feature value via the GUI. According to another embodiment, the medical imaging apparatus 300 may receive the user feature value corresponding to the user identification information from an external server.

The use environment feature value may include an intensity of illumination, a use location of a medical image, or the like. The intensity of illumination indicates an intensity of illumination of a location or place where the medical image is read. The use location of the medical image may be divided into an operating room, an examining room, an ambulance, a laboratory, or the like.

The use environment feature value may be obtained from information stored in the medical imaging apparatus 300, may be obtained from a sensor provided at the medical imaging apparatus 300, or may be obtained by receiving information about a use environment from an external apparatus. According to an embodiment, the medical imaging apparatus 300 may include an illumination sensor and may obtain an illumination value from a sensing value sensed by the illumination sensor. According to an embodiment, the medical imaging apparatus 300 may include a global positioning system (GPS), and may determine the use location of the medical image, based on location information obtained by the GPS. According to an embodiment, the medical imaging apparatus 300 may store information about a place where a corresponding apparatus is installed and may obtain information about the use location by using the stored information.

The apparatus feature value may include a display feature, processor performance, a manufacturer, a model name, or the like. The display feature may include a brightness feature of a display, a dynamic range feature, or the like. The apparatus feature value indicates features of an apparatus for reading a medical image. According to an embodiment, when a medical image processed by the processor 320 is transmitted to an external apparatus via the communicator, a feature of the external apparatus is expressed as the apparatus feature value.

The apparatus feature value may be obtained based on identification information of an apparatus. For example, the processor 320 may use an apparatus feature value stored to correspond to a serial number of the apparatus. As another example, the processor 320 may use an apparatus feature value stored to correspond to a manufacturer or a model name of the apparatus. For example, the storage 340 may store a type of the apparatus (e.g., a smartphone, a tablet PC, a desktop computer, a wearable device, or the like), a display feature, or the like with respect to the serial number or the model name of the apparatus.

The patient feature value includes a medical history of a patient. For example, the patient feature value may include a region of interest (ROI), a name of disease, a disease progress, or the like of the patient. When a medical image is an ultrasound image, the patient feature value may include TGC and LGC that are appropriate for the ROI of the patient. When the medical image is a CT image, the patient feature value may include WL and WW that are appropriate for the ROI of the patient.

The processor 320 may receive identification information about the patient from the input interface 310, and may obtain the patient feature value from the storage 340 or an external apparatus. As another example, the processor 320 may receive the patient feature value via the input interface 310.

The scan feature value may include an executed protocol, a type of ROI, a position of ROI, or the like. The type of ROI may be classified according to an organ corresponding to a ROI, whether the ROI moves, a type (a bone, blood, a membrane, or the like) of tissue of the ROI, or the like. The position of ROI may indicate information about in which organ a ROI is placed, a depth of the ROI, or the like.

Figure 5:
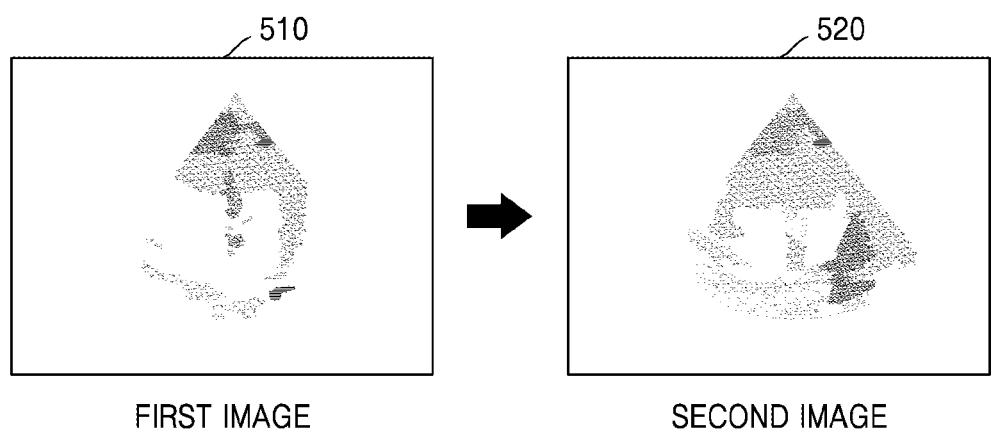
FIG. 5 illustrates medical images according to an embodiment.

FIG. 5 illustrates medical images according to an embodiment.

According to an embodiment, while a first image 510 is obtained by using a first value of a first parameter with respect to an input medical image and is displayed, when a first control signal of setting the first parameter as a second value is input, the processor 320 generates a second image 520 by setting the first parameter as the second value and outputs the second image 520 via the output interface 330. Also, the processor 320 not only performs a simple process of setting the first parameter as the second value but also calculates an optimization coefficient based on the first control signal and updates an optimization coefficient stored in the storage 340.

Figure 6:
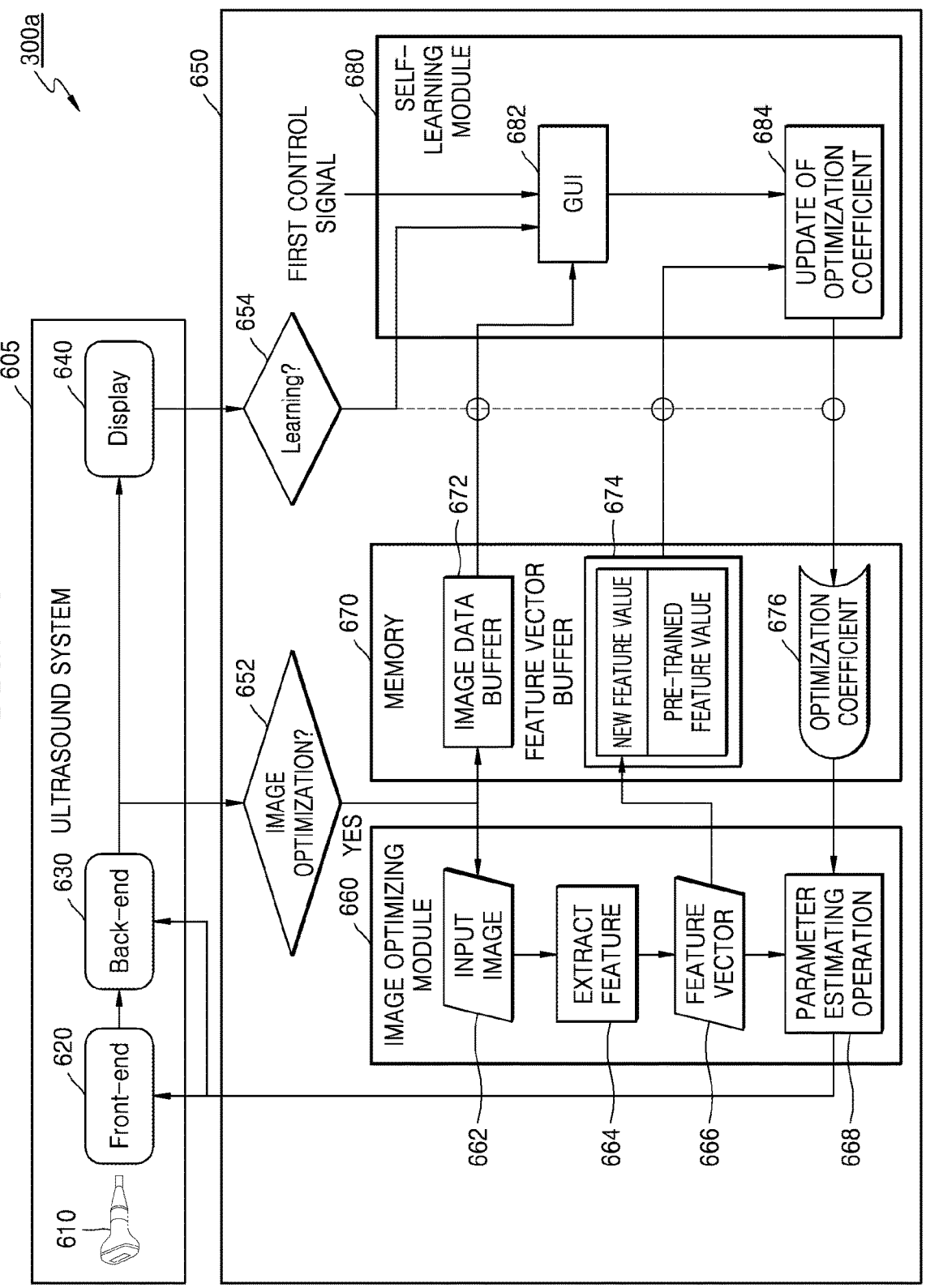
FIG. 6 is a diagram illustrating a configuration of a medical imaging apparatus according to an embodiment.

FIG. 6 is a diagram illustrating a configuration of a medical imaging apparatus 300a according to an embodiment.

According to an embodiment, the medical imaging apparatus 300a may include an ultrasound system 605 and a processor 650. The ultrasound system 605 and the processor 650 may be embodied in one body or may be separately embodied.

The ultrasound system 605 may include a probe 610 to output an ultrasound signal and detect an echo signal, a front-end 620 to process an analog signal output from the probe 610, and a back-end 630 to process a digital signal processed by the front-end 620 and deliver the digital signal, a display 640 to display an ultrasound image and a GUI view, and the processor 650.

The processor 650 may include an image optimizing module 660, a self-learning module 680, and a memory 670. The image optimizing module 660 estimates an optimal parameter with respect to an input medial image and feeds back the optimal parameter to the ultrasound system 605. The self-learning module 680 receives a user-input first control signal with respect to an output medical image, and updates the image optimizing module 660 in real time so as to output an optimal result according to user preference.

A medical image obtained via the probe 610 is displayed in real time on the display 640. When image optimization with respect to the displayed current medical image is requested by a user (operation 652), the image optimizing module 660 performs parameter estimation based on a feature vector.

The image optimizing module 660 extracts a feature vector 666 by extracting (operation 664) an image feature value from an input image 662. In this regard, the input image 662 and the feature vector 666 are respectively stored in an image data buffer 672 and a feature vector buffer 674 of the memory 670. The image optimizing module 660 performs an operation 668 of estimating a value of a parameter including a gain, DR, TGC, or the like from the feature vector 666 stored in the feature vector buffer 674 and an optimization coefficient 676 of the memory 670. For the operation 668 of estimating the value of the parameter, various methods including a linear least squares method, deep learning, or the like may be used. The estimated value of the parameter is fed back to the ultrasound system 605, and a medical image whose brightness, a dynamic range, or the like is changed due to a change in the value of the parameter is displayed on the display 640.

Also, according to an embodiment, the self-learning module 680 is provided to improve the image optimizing module 660 to operate an image optimizing function by applying user preference thereto. When a user requests execution of self-learning (operation 654), the self-learning module 680 performs self-learning for optimization. First, a GUI module 682 is executed to receive, from a user, an input of a user control signal with respect to a medical image generated based on the estimated value of the parameter. Image data stored in the image data buffer 672 of the memory 670 is input to the GUI module 682, and the GUI module 682 displays, on the display 640, multi-view images of various values of the parameter.

The image optimizing module 660 combines a parameter value with a pre-trained feature value and stores a combined value as a new feature value in the feature vector buffer 674, wherein the parameter value is based on user preference input via the GUI module 682 and the pre-trained feature value is stored in the feature vector buffer 674. The self-learning module 680 performs an optimization coefficient updating process 684 by using the new feature value stored in the feature vector buffer 674 and the pre-trained feature value that is preset in a factory during the manufacture, and stores the updated optimization coefficient 676 in the memory 670. The optimization coefficient updating process 684 is performed in real time and is applied when next image optimization is performed.

FIG. 7 illustrates a GUI view according to an embodiment.

The processor 320 may provide a GUI for receiving a first control signal of setting a parameter value. According to an embodiment, as illustrated in FIG. 7, the GUI view may display a medical image 712, and may include the GUI for receiving a first control signal of setting a parameter value. The GUI view may include a first area 710 and a second area 720.

The first area 710 displays a plurality of the medical images 712 generated by using candidate parameter values, and provides the GUI for receiving a first control signal of selecting one of the displayed plurality of medical images 712. For example, the first area 710 may include nine candidate medical images 712 generated by applying three candidate values with respect to a parameter 1 and three candidate values with respect to a parameter 2 to an input medical image.

The processor 320 may identify respective optimal parameter values of the parameter 1 and the parameter 2, and may determine a plurality of candidate values based on the optimal parameter values. For example, the processor 320 may determine a plurality of candidate values with respect to an optimal parameter value at a preset interval.

Also, the processor 320 may generate the candidate medical images 712 by applying the candidate values with respect to the parameter 1 and the parameter 2 to the input medical image. For example, when the parameter 1 is a gain and the parameter 2 is a DR index, the processor 320 may determine a preset number of candidate values with respect to a value of the gain, may determine a preset number of candidate values with respect to the DR index, and may generate the candidate medical images 712 by using the candidate values with respect to the gain and the DR index. For example, a first candidate medical image 712a is generated by applying a gain value of 48 and a DR index of 48 thereto, a second candidate medical image 712b is generated by applying a gain value of 50 and a DR index of 48 thereto, and a third candidate medical image 712c is generated by applying a gain value of 52 and a DR index of 48 thereto.

The processor 320 may identify a value of the parameter 1 and a value of the parameter 2, in response to a first control signal of selecting one of the candidate medical images 712. For example, when a user selects the second candidate medical image 712b, the processor 320 may identify the value of the parameter 1 to be 50 and the value of the parameter 2 to be 48.

According to an embodiment, the processor 320 may adjust the value of the parameter 1 and the value of the parameter 2, according to a selected position on the candidate medical image 712. For example, when the first control signal selects a position of an arrow 1 714 on the second candidate medical image 712b, the processor 320 may identify the value of the parameter 1 to be 50.5 and the value of the parameter 2 to be 48.5. According to the present embodiment, a parameter value may be finely adjusted in one candidate medical image 712, therefore, a user may further accurately designate a parameter value.

The second area 720 indicates a plurality of candidate values 722 with respect to a parameter 3 corresponding to a set of a plurality of values. The set of the plurality of values of the parameter 3 may be expressed as a graph. The parameter 3 may correspond to a TGC value, an LGC value, or the like. The second area 720 may include a plurality of candidate graphs 724. The processor 320 may generate an optimal graph of the parameter 3, based on a feature vector, and then may generate the plurality of candidate graphs 724 based on the optimal graph. In response to a first control signal of selecting one of a plurality of candidate values 722, the processor 320 may determine a selected candidate value 722 to be a value of the parameter 3.

According to an embodiment, the second area 720 may provide curve adjustment UIs 726a and 726b for changing a form of a graph of each candidate value 722. According to an embodiment, the curve adjustment UIs 726a and 726b may include icons 728a and 728b for changing a form or a curvature of a curve 724a, and when positions of the icons 728a and 728b are changed in response to a control signal, the curve adjustment UIs 726a and 726b may change the form or the curvature of the curve 724a to correspond to the changed positions of the icons 728a and 728b. According to an embodiment, the icons 728a and 728b may be moved on reference lines 729a and 729b.

According to an embodiment, only one of the first area 710 and the second area 720 may be provided to a GUI. Types of parameters that may be adjusted in the first area 710 or the second area 720 may be preset or may be determined according to user selection.

Arrangements of the first area 710 and the second area 720 illustrated in FIG. 7 may be an example, and in another embodiment, sizes, forms, designs, or the like of the first area 710 and the second area 720 may be changed.

According to an embodiment, the processor 320 may provide a GUI for inputting a feature value. For example, the GUI for inputting a feature value may be provided with a GUI for selecting a parameter value. The GUI for inputting a feature value may provide a UI for receiving an input of a user feature value, a use environment feature value, an apparatus feature value, a patient feature value, a scan feature value, or the like.

Figure 8:
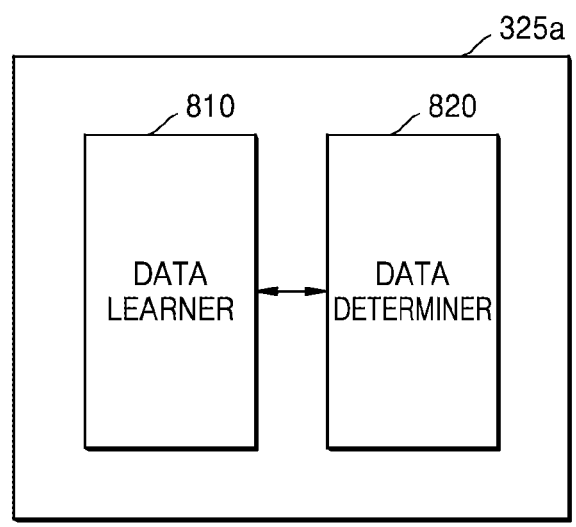
FIG. 8 is a block diagram of a neural network processor according to an embodiment.

FIG. 8 is a block diagram of a neural network processor 325a according to an embodiment.

Referring to FIG. 8, the neural network processor 325a according to an embodiment may include a data trainer 810 and a data determiner 820.

The data trainer 810 may learn a criterion for determining a situation. The data trainer 810 may learn a criterion about which data is to be used to determine a certain situation and about how to determine a certain situation by using data. The data trainer 810 may obtain data to be used in learning, may apply the obtained data to a data determination model to be described below, and thus may learn the criterion for determining a situation.

The data determiner 820 may determine a situation, based on data. The data determiner 820 may determine the situation, based on certain data, by using a trained data determination model. The data determiner 820 may obtain certain data, based on a criterion that is preset due to training, and may determine a certain situation, based on the certain data, by using the data determination model by using the obtained data as an input value. A resultant value output via the data determination model by using the obtained data as the input value may be used in updating the data determination model.

At least one of the data trainer 810 and the data determiner 820 may be embodied as at least one hardware chip and may be mounted in the medical imaging apparatus 300. For example, at least one of the data trainer 810 and the data determiner 820 may be embodied as a dedicated hardware chip for artificial intelligence (AI), or may be embodied as a part of a general-use processor (e.g., a central processing unit (CPU) or an application processor) or a graphic-dedicated processor (e.g., a graphics processing unit (GPU) and may be mounted in the medical imaging apparatus 300.

In this case, the data trainer 810 and the data determiner 820 may be mounted together in the medical imaging apparatus 300, or may be embodied separately in respective apparatuses. For example, one of the data trainer 810 and the data determiner 820 may be included in the medical imaging apparatus 300 and the other one may be included in a server. Also, the data trainer 810 and the data determiner 820 may communicate with each other in a wired or wireless manner, such that model information established by the data trainer 810 may be provided to the data determiner 820, and data input to the data determiner 820 may be provided, as additional training data, to the data trainer 810.

At least one of the data trainer 810 and the data determiner 820 may be embodied as a software module. When at least one of the data trainer 810 and the data determiner 820 is embodied as a software module (or a program module including instructions), the software module may be stored in a non-transitory computer-readable recording medium. In this case, one or more software modules may be provided by an operating system (OS) or a certain application. Alternatively, some of the one or more software modules may be provided by the OS and the rest of the one or more software modules may be provided by a certain application.

Figure 9:
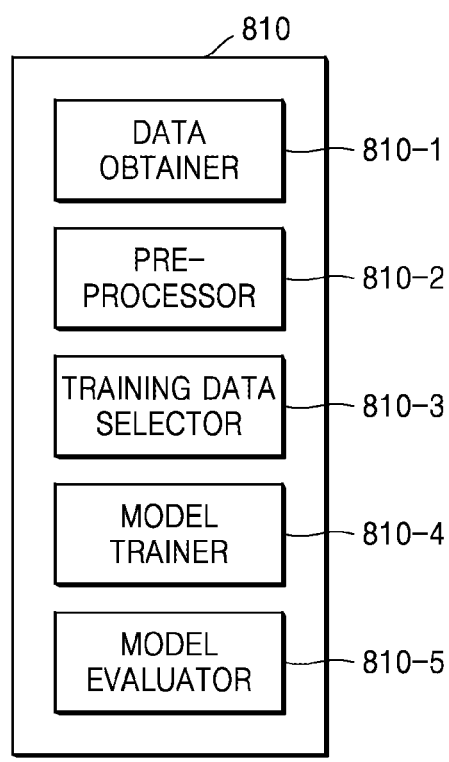
FIG. 9 is a block diagram illustrating a data learner according to an embodiment.

FIG. 9 is a block diagram illustrating the data trainer 810 according to an embodiment.

Referring to FIG. 9, the data trainer 810 according to an embodiment may include a data obtainer 810-1, a pre-processor 810-2, a training data selector 810-3, a model trainer 810-4, and a model evaluator 810-5.

The data obtainer 810-1 may obtain data necessary for determination of situation. The data obtainer 810-1 may obtain data required in training for determination of situation. For example, the data obtainer 810-1 may obtain raw data, a feature value, a first control signal, or the like to obtain a feature value vector.

The pre-processor 810-2 may pre-process the obtained data to make the obtained data used in training for determination of situation. The pre-processor 810-2 may process the obtained data to have a preset format so as to allow the model trainer 810-4 to use the obtained data in training for determination of situation.

The training data selector 810-3 may select, from among the pre-processed data, data required in training. The selected data may be provided to the model trainer 810-4.

The training data selector 810-3 may select, from among the pre-processed data, the data required in training, according to a preset criterion for determination of situation. Also, the training data selector 810-3 may select data according to a criterion that is preset via training by the model trainer 810-4 to be described below.

The model trainer 810-4 may learn a criterion about how to determine a situation, based on training data. Also, the model trainer 810-4 may learn a criterion about which training data is to be used to determine a situation Also, the model trainer 810-4 may train, by using training data, a data determination model to be used in determination of situation. In this case, the data determination model may be a pre-established model. For example, the data determination model may be a model that has been pre-established by receiving default training data (e.g., a sample image, or the like).

The data determination model may be established, in consideration of an application field of a determination model, an objective of training, a computing capability of an apparatus, or the like. The data determination model may be a model based on a neural network. For example, models including a deep neural network (DNN), a recurrent neural network (RNN), a bidirectional recurrent deep neural network (BRDNN), or the like may be used as the data determination model, but the present disclosure is not limited thereto.

According to various embodiments, when there are a plurality of pre-established data determination models, the model trainer 810-4 may determine, as a data determination model to train, a data determination model having a high relation between input training data and default training data. In this case, the default training data may be pre-classified according to types of data, and data determination models may be pre-established according to the types of data. For example, the default training data may be pre-classified according to various criteria including an area where training data is generated, a time when training data is generated, a size of training data, a genre of training data, a generator of training data, types of an object in training data, or the like.

Also, the model trainer 810-4 may train a data determination model by using a training algorithm including an error back-propagation algorithm, a gradient descent gradient descent, or the like.

Also, the model trainer 810-4 may train a data determination model by supervised learning using training data as an input value. Also, the model trainer 810-4 may train a data determination model by unsupervised learning in which a criterion for determination of situation is found by self-learning a type of data necessary for determination of situation without supervision. Also, the model trainer 810-4 may train a data determination model by reinforcement learning using a feedback about whether a result of determining a situation according to training is correct.

When a data determination model is trained, the model trainer 810-4 may store the trained data determination model. In this case, the model trainer 810-4 may store the trained data determination model in a memory of the medical imaging apparatus 300 including the data determiner 820. Alternatively, the model trainer 810-4 may store the trained data determination model in a memory of a server that is connected to the medical imaging apparatus 300 via a wired or wireless network.

In this case, the memory that stores the trained data determination model may also store, for example, a command or data related with at least one other component of the medical imaging apparatus 300. The memory may also store software and/or a program. The program may include, for example, a kernel, a middleware, an application programming interface (API), and/or an application program (or an application).

The model evaluator 810-5 may input evaluation data to a data determination model, and when a determination result output from the evaluation data does not satisfy a certain criterion, the model evaluator 810-5 may allow the model trainer 810-4 to train the data determination model again. In this case, the evaluation data may be preset data for evaluating a data determination model.

For example, when the number or a rate of the evaluation data whose determination result is not correct is greater than a preset threshold value, the determination result being from among determination results of the data determination model trained with respect to the evaluation data, the model evaluator 810-5 may evaluate that the certain criterion is not satisfied. For example, in a case where the certain criterion is defined as a rate of 2%, when the trained data determination model outputs incorrect determination results for at least 20 items of evaluation data among a total of 1000 items of evaluation data, the model evaluator 810-5 may evaluate that the trained data determination model is not appropriate.

When there are a plurality of trained data determination models, the model evaluator 810-5 may evaluate whether each of trained data determination models satisfies the certain criterion, and may determine a model to be a final data determination model, the model satisfying the certain criterion. In this case, when the model satisfying the certain criterion is plural in number, the model evaluator 810-5 may determine, as the final data determination model, one model or a certain number of models which are preset according to their respective high evaluation scores.

At least one of the data obtainer 810-1, the pre-processor 810-2, the training data selector 810-3, the model trainer 810-4, and the model evaluator 810-5 in the data trainer 810 may be embodied as at least one hardware chip and may be mounted in the medical imaging apparatus 300. For example, at least one of the data obtainer 810-1, the pre-processor 810-2, the training data selector 810-3, the model trainer 810-4, and the model evaluator 810-5 may be embodied as a dedicated hardware chip for AI, or may be embodied as a part of a general-use processor (e.g., a CPU or an application processor) or a graphic-dedicated processor (e.g., a GPU and may be mounted in the medical imaging apparatus 300.

In this case, the data obtainer 810-1, the pre-processor 810-2, the training data selector 810-3, the model trainer 810-4, and the model evaluator 810-5 may be mounted together in one apparatus, or may be embodied separately in respective apparatuses. For example, some of the data obtainer 810-1, the pre-processor 810-2, the training data selector 810-3, the model trainer 810-4, and the model evaluator 810-5 may be included in the medical imaging apparatus 300 and the others may be included in a server.

At least one of the data obtainer 810-1, the pre-processor 810-2, the training data selector 810-3, the model trainer 810-4, and the model evaluator 810-5 may be embodied as a software module. When at least one of the data obtainer 810-1, the pre-processor 810-2, the training data selector 810-3, the model trainer 810-4, and the model evaluator 810-5 is embodied as a software module (or a program module including instructions), the software module may be stored in a non-transitory computer-readable recording medium. In this case, one or more software modules may be provided by an OS or a certain application. Alternatively, some of the one or more software modules may be provided by the OS and the rest of the one or more software modules may be provided by a certain application.

Figure 10:
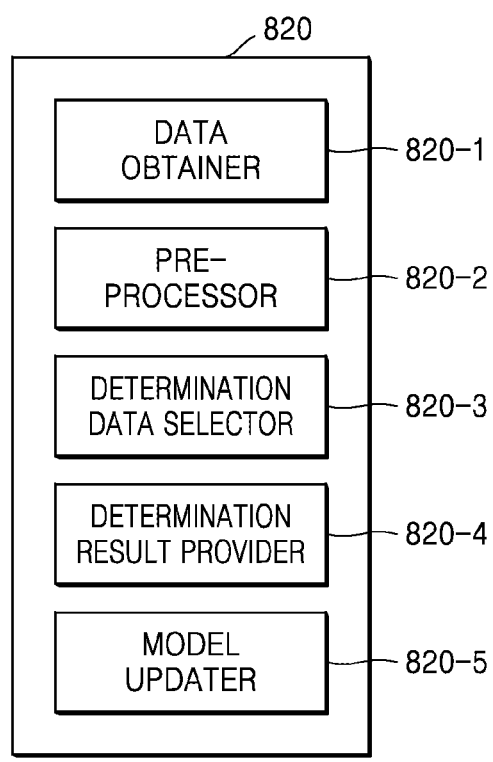
FIG. 10 is a block diagram illustrating a data determiner according to an embodiment.

FIG. 10 is a block diagram illustrating the data determiner 820 according to an embodiment.

Referring to FIG. 10, the data determiner 820 according to an embodiment may include a data obtainer 820-1, a pre-processor 820-2, a determination data selector 820-3, a determination result provider 820-4, and a model updater 820-5.

The data obtainer 820-1 may obtain data necessary for determination of situation, and the pre-processor 820-2 may pre-process the obtained data to make the obtained data used in determination of situation. The pre-processor 820-2 may process the obtained data to have a preset format so as to allow the determination result provider 820-4 to use the obtained data for determination of situation.

The determination data selector 820-3 may select, from among the pre-processed data, data necessary for determination of situation. The selected data may be provided to the determination result provider 820-4. The determination data selector 820-3 may select all or some of the pre-processed data, according to a preset criterion for determination of situation. Also, the determination data selector 820-3 may select data according to a criterion that is preset via training by the model trainer 810-4 described above.

The determination result provider 820-4 may determine a situation by applying the selected data to a data determination model. The determination result provider 820-4 may provide a determination result according to a determination objective with respect to the data. The determination result provider 820-4 may apply the selected data to the data determination model by using, as an input value, the data selected by the determination data selector 820-3. Also, the determination result may be determined by the data determination model.

The model updater 820-5 may allow the data determination model to be updated, based on evaluation of the determination result provided by the determination result provider 820-4. For example, the model updater 820-5 may allow the data determination model to be updated by the model trainer 810-4 by providing, to the model trainer 810-4, the determination result provided by the determination result provider 820-4.

At least one of the data obtainer 820-1, the pre-processor 820-2, the determination data selector 820-3, the determination result provider 820-4, and the model updater 820-5 in the data determiner 820 may be embodied as at least one hardware chip and may be mounted in the medical imaging apparatus 300. For example, at least one of the data obtainer 820-1, the pre-processor 820-2, the determination data selector 820-3, the determination result provider 820-4, and the model updater 820-5 may be embodied as a dedicated hardware chip for AI, or may be embodied as a part of a general-use processor (e.g., a CPU or an application processor) or a graphic-dedicated processor (e.g., a GPU and may be mounted in the medical imaging apparatus 300.

In this case, the data obtainer 820-1, the pre-processor 820-2, the determination data selector 820-3, the determination result provider 820-4, and the model updater 820-5 may be mounted together in one apparatus, or may be embodied separately in respective apparatuses. For example, some of the data obtainer 820-1, the pre-processor 820-2, the determination data selector 820-3, the determination result provider 820-4, and the model updater 820-5 may be included in the medical imaging apparatus 300 and the others may be included in a server.

At least one of the data obtainer 820-1, the pre-processor 820-2, the determination data selector 820-3, the determination result provider 820-4, and the model updater 820-5 may be embodied as a software module. When at least one of the data obtainer 820-1, the pre-processor 820-2, the determination data selector 820-3, the determination result provider 820-4, and the model updater 820-5 is embodied as a software module (or a program module including instructions), the software module may be stored in a non-transitory computer-readable recording medium. In this case, one or more software modules may be provided by an OS or a certain application. Alternatively, some of the one or more software modules may be provided by the OS and the rest of the one or more software modules may be provided by a certain application.

Figure 11:
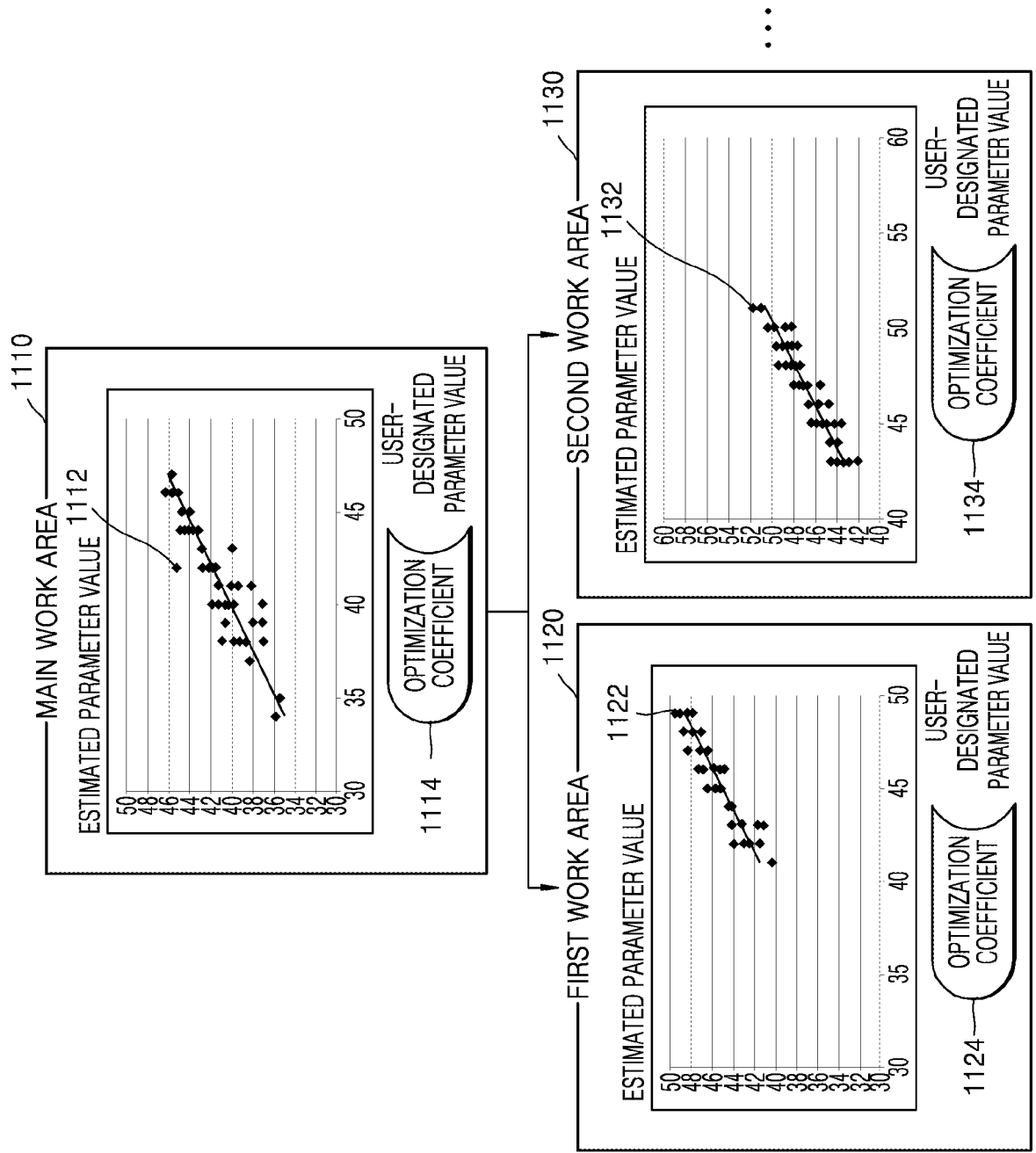
FIG. 11 illustrates an example of managing training data, according to an embodiment.

FIG. 11 illustrates an example of managing training data, according to an embodiment.

According to an embodiment, the medical imaging apparatus 300 may independently manage training data and an optimization coefficient with respect to a preset feature value. The preset feature value may be at least one of a user feature, a use environment feature, an apparatus feature, a patient feature, and a scan control feature. For example, the medical imaging apparatus 300 may independently manage an optimization coefficient according to each of users. To do so, the medical imaging apparatus 300 may independently manage training data according to each of users, and may calculate an optimization coefficient based on training data of each of users. When the optimization coefficient and the training data are managed according to each of users, the optimization coefficient and the training data may be separately managed according to user identification information.

The medical imaging apparatus 300 may manage the training data and the optimization coefficient by allocating first and second work areas 1120 and 1130 for the preset feature value to the storage 340, the first and second work areas 1120 and 113 being independent from each other. FIG. 11 illustrates training data 1112 where an estimated parameter value and a user-designated parameter value in response to a first control signal are matched. According to an embodiment, the medical imaging apparatus 300 may allocate a main work area 1110, the first work area 1120, and the second work area 1130 to the storage 340. The main work area 1110 may store and manage the training data 1112 and an optimization coefficient 1114 regardless of a feature value. The first work area 1120 may store and manage training data 1122 and an optimization coefficient 1124 for a first user. The second work area 1130 may store and manage training data 1132 and an optimization coefficient 1134 for a second user. In response to an input of a first control signal with respect to the first user, the processor 320 stores corresponding training data in the first work area 1120, and updates the optimization coefficient 1124, based on the training data in the first work area 1120. In response to an input of the first control signal with respect to the second user, the processor 320 stores corresponding training data in the second work area 1130, and updates the optimization coefficient 1134, based on the training data in the second work area 1130. The main work area 1110 may include pre-trained data and new training data, and the first work area 1120 and the second work area 1130 may each include new training data.

Figure 12:
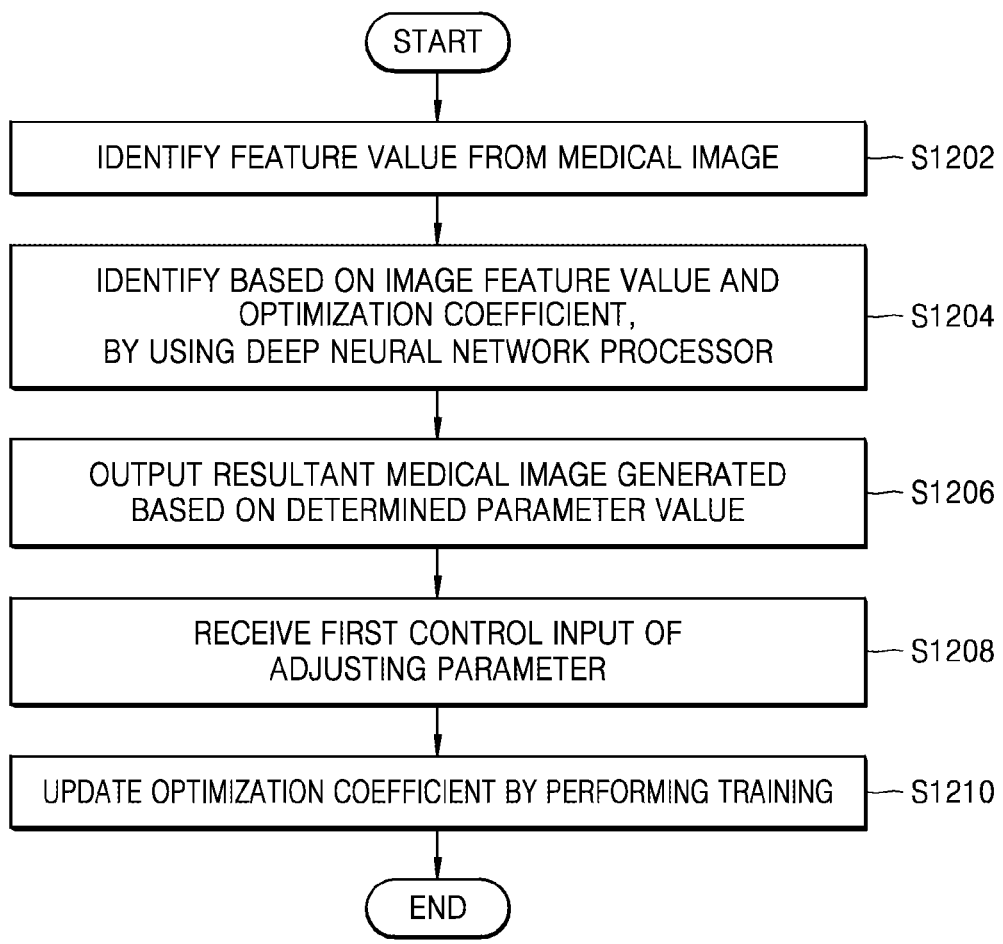
FIG. 12 is a flowchart of a medical imaging apparatus control method according to an embodiment.

FIG. 12 is a flowchart of a medical imaging apparatus control method according to an embodiment.

The medical imaging apparatus control method according to the present embodiment may be performed by one of various medical imaging apparatuses. In the present embodiment, it is assumed that the medical imaging apparatus 300 according to the one or more embodiments performs the medical imaging apparatus control method, but the present embodiment is not limited thereto. The one or more embodiments of the medical imaging apparatus 300 which are disclosed in the present disclosure may be applied to the medical imaging apparatus control method, and one or more embodiments of the medical imaging apparatus control method may be applied to the medical imaging apparatus 300.

The medical imaging apparatus 300 identifies a feature value from a medical image (S1202). The medical imaging apparatus 300 may obtain an image feature value from the medical image.

Next, the medical imaging apparatus 300 may identify a parameter value based on the image feature value and an optimization coefficient, by using the neural network processor 325 (e.g., a deep neural network processor) (S1204).

The medical imaging apparatus 300 may output a resultant medical image generated based on the identified parameter value (S1206). For example, the medical imaging apparatus 300 may display the resultant medical image or may transmit the resultant medical image to an external apparatus via the communicator.

The medical imaging apparatus 300 may receive a first control input of adjusting the parameter value (S1208), and may set a parameter value based on the first control input.

Also, the medical imaging apparatus 300 may update the optimization coefficient by using the parameter value as training data, the parameter value being set in response to the first control input (S1210).

According to the embodiments, it is possible to improve a function of automatically setting parameters in a medical imaging apparatus.

Also, according to the embodiments, it is possible to automatically identify an appropriate parameter, in consideration of a user, a use environment, an apparatus used by the user, patient information, a protocol, or the like.

Also, according to the embodiments, it is possible to decrease a need for development manpower, a development period, and development costs of a medical imaging apparatus by simplifying initial settings of the medical imaging apparatus.

The embodiments may be implemented in a software program including instructions stored in a computer-readable storage medium.

The computer is a device capable of calling the stored instructions from the storage medium and operating according to the embodiments in accordance with the called instructions, and may include the ultrasound diagnosis apparatus according to the embodiments.

The computer-readable storage medium may be provided in the form of a non-transitory storage medium. Here, the term 'non-transitory' means that the storage medium is tangible and does not refer to a transitory electrical signal, but does not distinguish that data is stored semi-permanently or temporarily on the storage medium.

Furthermore, the medical imaging apparatus and the medical imaging apparatus control method according to the embodiments may be provided in a computer program product. The computer program product may be traded between a seller and a purchaser as a commodity.

The computer program product may include a software program and a computer-readable storage medium having stored thereon the software program. For example, the computer program product may include a product (e.g. a downloadable application) in a software program distributed electronically through a manufacturer of the medical imaging apparatus or an electronic market (e.g., Google Play Store and App Store). For electronic distribution, at least a part of the software program may be stored on the storage medium or may be generated temporarily. In this case, the storage medium may be a storage medium of a server of the manufacturer, a server of the electronic market, or a relay server for temporarily storing the software program.

The computer program product may include a storage medium of a server or a storage medium of a terminal, in a system including the server and the terminal (e.g., the ultrasound diagnosis apparatus). Alternatively, when there is a third device (e.g., a smartphone) that communicates with the server or the terminal, the computer program product may include a storage medium of the third device. Alternatively, the computer program product may include a software program that is transmitted from the server to the terminal or the third device or from the third device to the terminal.

In this case, one of the server, the terminal, and the third device may perform the method according to the embodiments by executing the computer program product. Alternatively, at least two of the server, the terminal, and the third device may divide and perform the method according to the embodiments by executing the computer program product.

For example, the server (e.g., a cloud server, an AI server, or the like) may execute the computer program product stored in the server, thereby controlling the terminal to perform the method according to the embodiments, the terminal communicating with the server.

As another example, the third device may execute the computer program product, thereby controlling the terminal to perform the method according to the embodiments, the terminal communicating with the terminal. In detail, the third device may remotely control the ultrasound diagnosis apparatus, thereby controlling the ultrasound diagnosis apparatus to irradiate an ultrasound signal to an object and to generate an image of an inside part of the object, based on information of a signal reflected from the object, As another example, the third device may directly perform, by executing the computer program product, the method according to the embodiments based on a value input from an auxiliary device (e.g., a probe of a medical apparatus). In detail, the auxiliary device may irradiate an ultrasound signal to an object and may obtain an ultrasound signal reflected from the object. The third device may receive an input of signal information about the reflected ultrasound signal from the auxiliary device, and may generate an image of an inside part of the object, based on the input signal information.

When the third device executes the computer program product, the third device may download the computer program product from the server, and may execute the downloaded computer program product. Alternatively, the third device may perform the method according to the embodiments by executing a pre-loaded computer program product.

What is claimed is:

1. A medical imaging apparatus comprising:
a storage configured to store training data and an optimization coefficient; at least one processor configured to identify at least one image feature value from an input medical image, and to identify a value of at least one parameter of the medical imaging apparatus, based on the at least one image feature value and the optimization coefficient, by using a neural network processor;

an output interface configured to output a resultant image generated based on the value of the at least one parameter; and an input interface configured to receive a first control input of adjusting the value of the at least one parameter, wherein the at least one processor is further configured to update the optimization coefficient by performing training using the training data and the first control input, wherein the at least one processor is further configured to provide a graphical user interface (GUI) configured to receive the first control input, wherein the at least one parameter comprises a first parameter corresponding to a set of a plurality of values, wherein an interface view of the GUI comprises a plurality of candidate graphs indicating the set of the plurality of values corresponding to the first parameter, wherein, in response to a first control signal of selecting one of the plurality of candidate graphs, the at least one processor is further configured to identify the selected candidate graph as the value of the at least one parameter, and wherein the interface view comprises a curve adjustment UI for changing a form or a curvature of the plurality of candidate graphs.

2. The medical imaging apparatus of claim 1, wherein the at least one processor is further configured to identify the value of the at least one parameter by using a use environment feature value of the medical imaging apparatus as an input value to be input to the neural network processor.

3. The medical imaging apparatus of claim 1, wherein the at least one processor is further configured to identify the value of the at least one parameter by using an apparatus feature value corresponding to the medical imaging apparatus as an input value to be input to the neural network processor.

4. The medical imaging apparatus of claim 1, wherein the at least one processor is further configured to identify the value of the at least one parameter by using a patient feature value corresponding to an object of the medical imaging apparatus as an input value to be input to the neural network processor.

5. The medical imaging apparatus of claim 1, wherein the at least one processor is further configured to identify the value of the at least one parameter by using a scan control feature value of the medical imaging apparatus as an input value to be input to the neural network processor, wherein the scan control feature value comprises at least one of a protocol, a type of a region of interest (ROI), and a position of the ROI, or a combination thereof.

6. The medical imaging apparatus of claim 1, wherein the interface view comprises a plurality of candidate medical images generated by using respective candidate values with respect to the at least one parameter, and wherein, in response to the first control input of selecting one of the plurality of candidate medical images, the at least one processor is further configured to identify a candidate value as the value of the at least one parameter, the candidate value corresponding to the selected candidate medical image.

7. The medical imaging apparatus of claim 1, wherein the optimization coefficient comprises respective optimization coefficients with respect to a plurality of values of a first feature, wherein the first feature is one of a user feature, a use environment feature, an apparatus feature, a patient feature, and a scan control feature.

8. The medical imaging apparatus of claim 1, wherein the at least one processor is further configured to store, in the storage, the updated optimization coefficient, and to store, as the training data in the storage, the at least one image feature value and the at least one parameter which corresponds to the first control input.

9. The medical imaging apparatus of claim 1, wherein the at least one processor is further configured to identify the value of the at least one parameter by using at least one user feature value of the medical imaging apparatus as an input value to be input to the neural network processor.

10. A medical imaging apparatus control method comprising:

identifying at least one image feature value from an input medical image;

identifying a value of at least one parameter of a medical imaging apparatus, based on the at least one image feature value and an optimization coefficient, by using a neural network processor;

outputting a resultant image generated based on the value of the at least one parameter;

receiving a first control input of adjusting the value of the at least one parameter;

updating the optimization coefficient by performing training using training data and the first control input; and providing a graphical user interface (GUI) configured to receive the first control input, wherein the at least one parameter comprises a first parameter corresponding to a set of a plurality of values, wherein an interface view of the GUI comprises a plurality of candidate graphs indicating the set of the plurality of values corresponding to the first parameter, wherein the medical imaging apparatus control method further comprises, in response to a first control signal of selecting one of the plurality of candidate graphs, identifying the selected candidate graph as the value of the at least one parameter, and wherein the interface view comprises a curve adjustment UI for changing a form or a curvature of the plurality of candidate graphs.

11. The medical imaging apparatus control method of claim 10, further comprising identifying the value of the at least one parameter by using a use environment feature value of the medical imaging apparatus as an input value to be input to the neural network processor.

12. The medical imaging apparatus control method of claim 10, further comprising identifying the value of the at least one parameter by using an apparatus feature value corresponding to the medical imaging apparatus as an input value to be input to the neural network processor.

13. The medical imaging apparatus control method of claim 10, further comprising identifying the value of the at least one parameter by using a patient feature value corresponding to an object of the medical imaging apparatus as an input value to be input to the neural network processor.

14. The medical imaging apparatus control method of claim 10, further comprising identifying the value of the at least one parameter by using a scan control feature value of the medical imaging apparatus as an input value to be input to the neural network processor, wherein the scan control feature value comprises at least one of a protocol, a type of a region of interest (ROI), and a position of the ROI, or a combination thereof.

15. The medical imaging apparatus control method of claim 10, wherein
the interface view comprises a plurality of candidate medical images generated by using respective candidate values with respect to the at least one parameter, and
wherein the medical imaging apparatus control method further comprises, in response to the first control input of selecting one of the plurality of candidate medical images, identifying a candidate value as the value of the at least one parameter, the candidate value corresponding to the selected candidate medical image.

16. The medical imaging apparatus control method of claim 10, wherein the optimization coefficient comprises respective optimization coefficients with respect to a plurality of values of a first feature,
wherein the first feature is one of a user feature, a use environment feature, an apparatus feature, a patient feature, and a scan control feature.

17. The medical imaging apparatus control method of claim 10, further comprising identifying the value of the at least one parameter by using at least one user feature value of the medical imaging apparatus as an input value to be input to the neural network processor.

18. A computer program product comprising a non-transitory computer-readable storage medium storing computer program codes for performing a medical imaging apparatus control method, the medical imaging apparatus control method comprising:
identifying at least one image feature value from an input medical image;
identifying a value of at least one parameter of a medical imaging apparatus, based on the at least one image feature value and an optimization coefficient, by using a neural network processor;
outputting a resultant image generated based on the value of the at least one parameter;
receiving a first control input of adjusting the value of the at least one parameter; and
updating the optimization coefficient by performing training using training data and the first control input,
wherein the at least one parameter comprises a first parameter corresponding to a set of a plurality of values,
wherein an interface view comprises a plurality of candidate graphs indicating the set of the plurality of values corresponding to the first parameter,
wherein the medical imaging apparatus control method further comprises, in response to a first control signal of selecting one of the plurality of candidate graphs, identifying the selected candidate graph as the value of the at least one parameter, and
wherein the interface view comprises a curve adjustment UI for changing a form or a curvature of the plurality of candidate graphs.

\* \* \* \* \*